United States Patent
Grodzki et al.

(10) Patent No.: US 10,663,547 B2
(45) Date of Patent: May 26, 2020

(54) AUTOMATIC DETECTION AND SETTING OF MAGNETIC RESONANCE PROTOCOLS BASED ON READ-IN IMAGE DATA

(71) Applicant: Siemens Healthcare GmbH, Erlangen (DE)

(72) Inventors: David Grodzki, Erlangen (DE); Donald Hardie, Moehrendorf (DE); Katharina Hesels, Erlangen (DE); Lars Lauer, Neunkirchen (DE); Edgar Mueller, Heroldsbach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/051,919

(22) Filed: Aug. 1, 2018

(65) Prior Publication Data

US 2019/0041478 A1    Feb. 7, 2019

(30) Foreign Application Priority Data

Aug. 1, 2017  (DE) .................. 10 2017 213 222

(51) Int. Cl.
| | | |
|---|---|---|
| *G01R 33/54* | (2006.01) | |
| *A61B 5/00* | (2006.01) | |
| *G01R 33/56* | (2006.01) | |
| *A61B 5/055* | (2006.01) | |
| *G06N 3/04* | (2006.01) | |
| *G06N 3/12* | (2006.01) | |
| *G06N 3/08* | (2006.01) | |

(52) U.S. Cl.
CPC ............ *G01R 33/546* (2013.01); *A61B 5/004* (2013.01); *A61B 5/0037* (2013.01); *A61B 5/055* (2013.01); *G01R 33/543* (2013.01); *G01R 33/5608* (2013.01); *A61B 2576/02* (2013.01); *G06N 3/0454* (2013.01); *G06N 3/08* (2013.01); *G06N 3/126* (2013.01)

(58) Field of Classification Search
CPC ................ G01R 33/546; G01R 33/543; G01R 33/5608; G01R 33/56; A61B 2576/02; A61B 5/004; A61B 5/0037; A61B 5/055; G06N 3/126; G06N 3/0454; G06N 3/08
See application file for complete search history.

(56) References Cited

U.S. PATENT DOCUMENTS

2005/0154292 A1  7/2005  Tank
2015/0260819 A1  9/2015  Lauer et al.

FOREIGN PATENT DOCUMENTS

DE      102014209764 A1   11/2015

*Primary Examiner* — Christopher Wait
(74) *Attorney, Agent, or Firm* — Schiff Hardin LLP

(57) ABSTRACT

In a method and apparatus for determining measurement protocol parameters of a magnetic resonance (MR) image, a first MR image exhibiting first contrast properties, is read into a computer and at least one first contrast ratio is determined in the computer from the first contrast properties. The computer then determines the measurement protocol parameters dependent on the at least one first contrast ratio, in order to generate a second MR image exhibiting second contrast properties such that the second contrast properties approximate, as closely as possible, to the first contrast properties. The measurement protocol parameters are presented as an output from the computer.

14 Claims, 7 Drawing Sheets

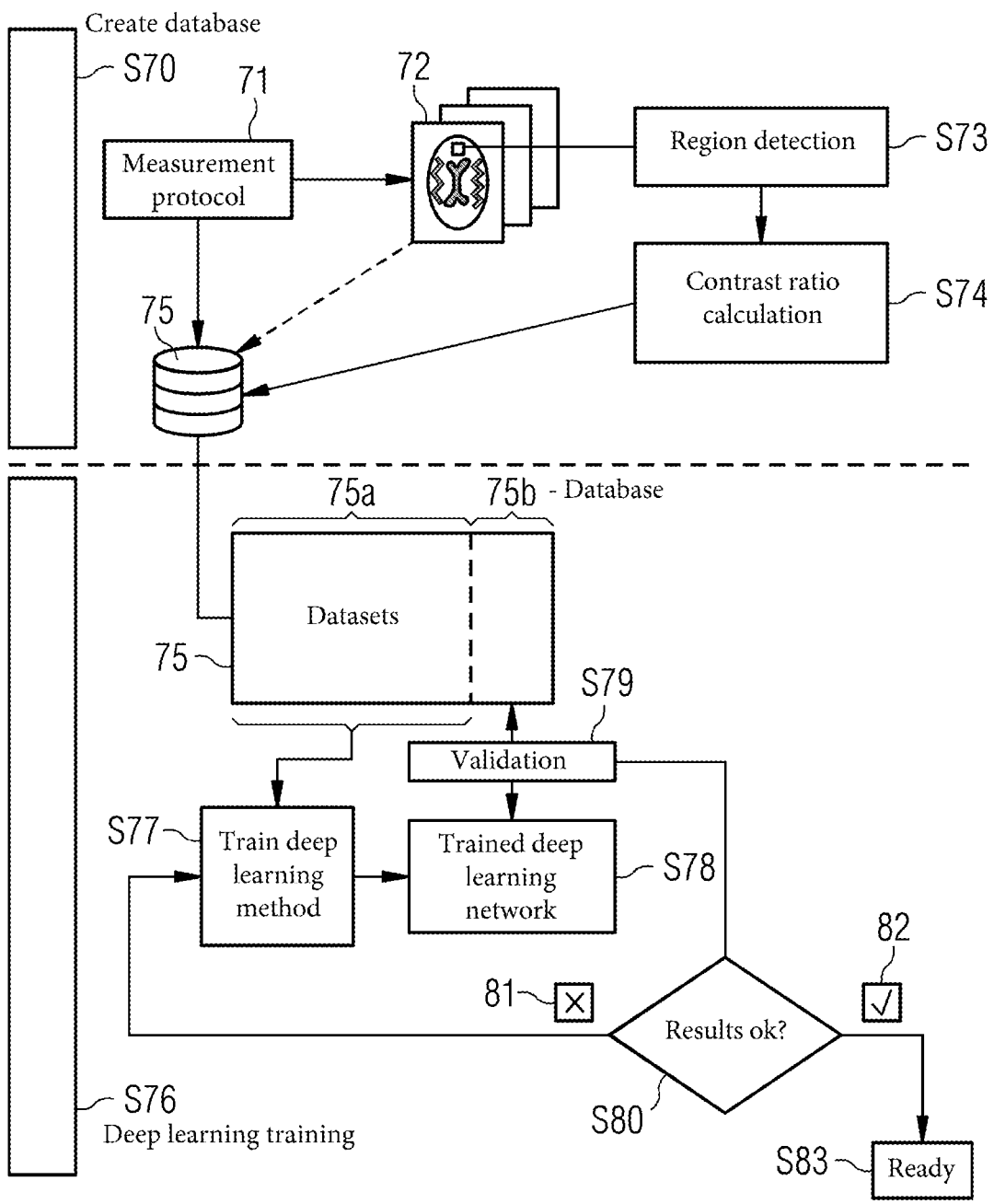

AUTOMATIC DETECTION AND SETTING OF MAGNETIC RESONANCE PROTOCOLS BASED ON READ-IN IMAGE DATA

BACKGROUND OF THE INVENTION

Field of the Invention

The present invention concerns a method and magnetic resonance (MR) apparatus for automatically detecting and setting measurement protocols for the MR apparatus on the basis of information obtained from MR image data that have been read into a control computer of the MR apparatus.

Description of the Prior Art

One of the great strengths of magnetic resonance imaging compared to other imaging modalities such as CT, X-ray and ultrasound is the excellent soft tissue contrast and the vast contrast range that can be represented by an MRT (magnetic resonance tomography) system. This strength, however, leads to a high level of complexity in terms of the MR imaging and the measurement parameters available for selection by the operator/technician, also known as measurement protocol parameters. In general, it is possible for only experienced and well-trained specialist personnel to produce MR protocols or to selectively modify an existing protocol. A further complicating factor is that MR image acquisitions are generally only weighted and are not quantitative with regard to an absolute standard, and consequently the result may be dependent on a large number of parameters, such as MR system configurations (field strength, number of channels, local coils, gradient values), as well as the patient.

Due to this complexity, the protocols used for an MR measurement (scan) are in most cases stored in a database and are geared to the local specifications and preferences of the clinic or radiologist. This database is mostly created by service personnel or a very experienced person during the MR system installation, and may be based on example images or the protocols of a comparable scanner. It may nevertheless be necessary or desirable to adapt the contrasts for certain measurements, e.g. when a patient possesses images acquired previously by a different clinic or hospital, or when it is necessary to find an answer to an unusual issue.

SUMMARY OF THE INVENTION

An object of the present invention is to provide a method for setting MR measurement protocols that operates in an automated manner without well-trained operating staff.

In the method for determining measurement protocol parameters of an MR image in accordance with the invention, a first MR image exhibiting first contrast properties is read into a control computer of an MR apparatus with which a current examination is to be conducted. At least one first contrast ratio is determined in the computer from the first contrast properties. Taking the at least one first contrast ratio into account, measurement protocol parameters are determined in the computer that are used to generate, by simulation, a second MR image exhibiting second contrast properties, with the second contrast properties approximating as closely as possible to the first contrast properties. The measurement protocol parameters are then emitted as electronic control signals for operating the MR apparatus (i.e., the scanner thereof) according to those parameters.

In this method, the first MR image is typically part of an existing MR image dataset that is read into the control computer and evaluated therein. The image dataset is preferably in a DICOM or similar format used in clinical tomographic imaging, which can be fed into the computer via a suitable interface. Alternatively, it is possible to use measurement data at an earlier processing stage in order initially to generate a two-dimensional image, which then represents the starting point for the described method. The goal of reading in the dataset is to ascertain and store all usable information.

According to the invention, a suitably MR measurement protocol is determined by an algorithm on the basis of the ascertained image information. This measurement protocol is produced for a particular MR apparatus for the purpose of generating an MR contrast that is at least equivalent in quality to that present in the first image.

Determining the at least one first contrast ratio from the first contrast properties may be accomplished, for example, on the basis of at least two first image areas, the image areas being assigned in each case to a different region from a list of regions of anatomical features comprising at least two different regions which are located in the first MR image. In this case the measurement protocol parameters are then selected such that the at least one first contrast ratio compared by region is as similar as possible to the at least one second contrast ratio determined from the second MR image.

In the evaluation of the MR contrast properties for the purpose of assigning anatomical regions of the first image, it is possible, for example, to apply pattern recognition methods or inputs by the user, or to use a method that represents a combination of both approaches. Landmark detection algorithms are an example well-known to those skilled in the art.

With these approaches, it is possible to detect such body and tissue regions that exhibit distinctive contrasts, or contrast ratios, in MR images. Thus, for example, $T_1$ contrasts (cerebrospinal fluid dark) can easily be differentiated from $T_2$ contrasts (cerebrospinal fluid bright) in images of the head. As a result of the combination of contrast ratio properties with the assignment to anatomical regions, inferences can be made directly to parts of the measurement protocol (e.g. the contrast setting), thereby enabling the number of free parameters of the measurement protocol settings to be reduced.

Furthermore, the assignment of the first image areas to the list of regions may be realized by the use of a deep-learning method.

A known strength of deep-learning methods (algorithms) is the detection of properties and making a binary assignment to categories. A classic example of machine learning is the task of correctly assigning images in which handwritten digits between '0' and '9' are represented. A dataset which frequently used for testing machine learning methods is the dataset known as the "Modified National Institute of Standards and Technology" database (MNIST). Such a deep-learning method may be implemented with the use of numerous libraries known to those skilled in the art, for example "TensorFlow" (C++, Python) from Google, Caffe from the Berkeley Vision and Learning Center (BVLC), Torch (C, Lua) and the Torchnet Facebook framework based thereon, or Microsoft Cognitive Toolkit (C++). Solving the assignment problem of MNIST is a typical example of the functioning on such libraries.

In an embodiment of the invention, such a library is used to perform the assignment of image areas to regions (e.g. anatomical regions such as cerebrospinal fluid, white substance, gray substance, etc.).

It is furthermore possible for the measurement protocol parameters to be determined with the use of a deep-learning method.

The deep-learning method may also use a first database that includes measurement protocol parameters, contrast properties and information relating to anatomical regions.

In this embodiment, the first contrast properties are evaluated by a deep-learning network. To that end, this network is initially trained via a database. The database used for this purpose is characterized by both the measurement protocols and the properties of the images, for example the contrast properties and/or the contrast ratios of different regions, being stored therein for a sufficiently large quantity of MR image datasets. In a deep-learning approach, this database is evaluated by a computer such that it "learns" the contrasts in connection with the protocols, and so is able to emit the necessary measurement protocol parameters for a new required contrast, as an output. It is also possible for the measurement protocol parameters to be determined by a simulation approach in which third MR images and third contrast properties are simulated iteratively for different measurement protocol parameters, until the third contrast properties approximate to the first contrast properties as closely as possible to.

With the simulation approach, it is possible for the Bloch equations to be solved in order to simulate the third MR images and the third contrast properties, and knowledge of at least the $T_1$ or $T_2$ time of anatomical regions identified in the first MR image is used.

In this case, assumed physical values or physical values actually measured on a patient ($T_1$, $T_2$, $T_2^*$, spin density, ... ) may be used in order to calculate complete MR images or contrast properties for different MR protocol settings, or else to calculate only the contrast ratios. In the simplest embodiment, the Bloch equations may be analytically or numerically solved 0-dimensionally without spatial information. In more complex methods, it is also conceivable to take the spatial dependence into account generally or with increasing specificity such as with ray tracing methods.

The results of the simulation are then compared with the first contrast properties or the calculated first contrast ratio. The comparison may be referred to in the iteration step in order to decide how to proceed further for the purpose of finding a strategy based on the previous results for the (test) measurement protocol parameters, in order to determine how to vary the measurement protocol parameters in the next iteration step in order to improve the result. Known optimization algorithms, for example a genetic algorithm, may be applied in this case.

Background knowledge, for example usage statistics of MR systems in measurements conducted on different anatomical regions or measurement methods, or statistics in relation to clinical findings/medical histories, may also be assimilated into the method in order to determine start values for the (test) measurement protocol parameters. This may advantageously be used in order to choose the first test measurement protocol parameters in the simulation step.

It is also possible for a measurement protocol for generating the second MR image to be produced in an automated manner from the determined measurement protocol parameters.

This approach enables the user of the MR system to obtain a complete measurement protocol directly on the basis of the determined parameters. This complete measurement protocol may be applied directly or may be modified according to the wishes of the user prior to the application.

It is furthermore possible for at least some of the measurement protocol parameters to be determined from meta information that are available for the first MR image. Such meta information may be easily used, for example, when the data of the first MR image are present in the DICOM format or a similar format used in clinical cross-sectional MRI CT imaging. In this case, "quantitative" values of the measurement may be read in, such as FOV, number of slices, MR system used, and MR system configuration, position, rotational alignment, windowing settings, pre-pulses. This is particularly productive and simple in the case of DICOM-like first image datasets.

A protocol name of an imaging sequence by which the first MR image was generated may also be used for determining the measurement protocol parameters.

The protocol name may be present, for example, in the form of a file name of the first MR image. Information relating to the contrast (for example the weighting, in other words e.g. $T_1$- or $T_2$-weighted measurement) and further measurement protocol parameters is often included in the protocol name. This information may provide reference points for producing the measurement protocol parameters and/or restrict the degrees of freedom of the search parameters or their value range. Likely measurement protocols may also be inferred on the basis of issues or case histories recorded in the protocol name, and in this way the possible options for measurement protocol parameters may be limited.

It is also possible that, when the first MR image is read in, this image is digitized from a printout or a screen display.

The digitization may also be realized by a photograph (e.g. taken by means of a smartphone) of a printed MR image or an MR image displayed on a screen. In a further embodiment variant, it is also possible to scan in an image dataset that is printed on film.

It is further possible for measurement protocol parameters to be determined for a second MR system, which was not used for generating the first MR image.

For the users of MR systems, this affords the advantage that clinical findings for a patient that were recorded using a different MR system, e.g. in a different hospital at a different time, may be more easily compared with the present condition of the patient.

Determining measurement protocol parameters may also be at least one of the following parameters: field of view, number of slices, MR system used, configuration of the MR system, position of the imaging volume, rotation of the imaging volume, rotational alignment, windowing setting, pulses, pre-pulses.

The present invention also encompasses a magnetic resonance apparatus having an MR data acquisition scanner operated by control computer, wherein the control computer is configured to implement any or all embodiments of the method according to the invention as described above.

The present invention also encompasses a non-transitory, computer-readable data storage medium encoded with programming instructions that, when loaded into a computer or computer system of a magnetic resonance apparatus, cause the computer or computer system to operate the magnetic resonance apparatus so as to implement any or all embodiments of the method according to the invention, as described above.

BRIEF DESCRIPTION OF THE DRAWINGS

FIG. 7 illustrates the process for providing a deep-learning network that is suitable for determining measurement protocol parameters for an MR image.

DESCRIPTION OF THE PREFERRED EMBODIMENTS

In the figures, like reference signs designate like or similar elements. Furthermore, the figures constitute schematic representations of different embodiment variants of the invention. The elements depicted in the figures are not necessarily represented true to scale and rather are reproduced in such a way that the function and purpose of the illustrated elements are rendered understandable. The connections shown between functional units or other elements in the figures may also be implemented as indirect connections, in which case a connection may be realized as wireless or hardwired. Functional units may be implemented as hardware, software or as a combination of hardware and software.

Figure 1:
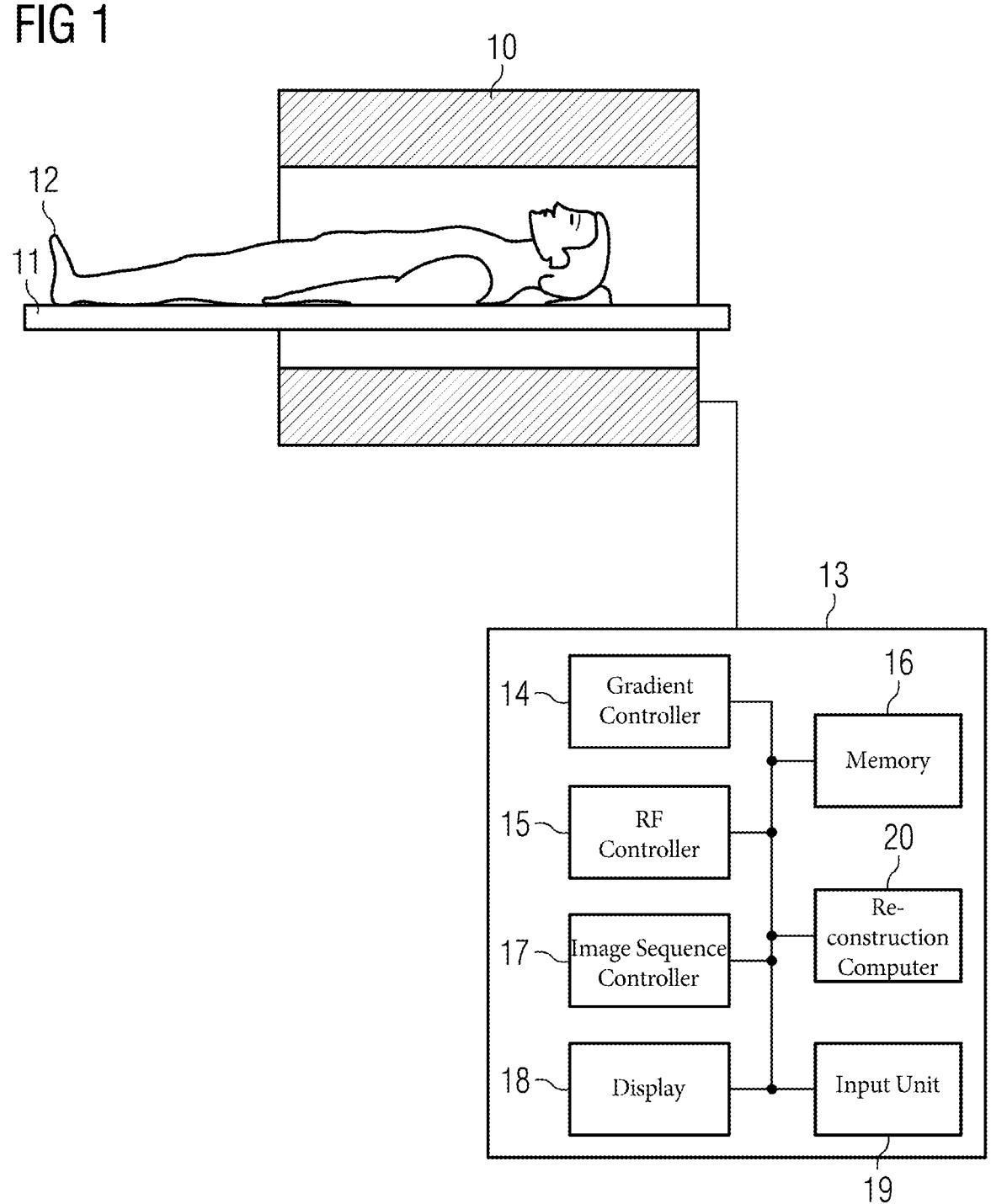
FIG. 1 schematically shows an MR apparatus with which the method according to the invention may be performed.

FIG. 1 schematically shows an MR system by which an automatic detection and setting of MR protocols on the basis of read-in image data is possible according to the invention. The magnetic resonance system has a scanner 10 with a basic field magnet that generates a polarization field $B_0$. An examination subject is arranged on a bed 11, and represents the examination object 12 that is advanced into an isocenter of the scanner 10 in order to acquire spatially encoded magnetic resonance signals of the examination object 12. By radiating radio-frequency pulses and switching magnetic field gradients, certain nuclear spins in the examination object 12 are given a magnetization that deflects the nuclear spins from the field lines of the polarization field $B_0$. This leads to a deflection of the nuclear spins from the steady state, and the currents induced in reception coils, as the nuclear spins relax and return to the steady state, are detected as magnetic resonance signals, which can then be transformed into image data. The general principle of operation for generating MR images based on the detection of magnetic resonance signals is well-known to those skilled in the art, so a more detailed description is not necessary herein.

The magnetic resonance system has a control computer 13 that controls the MR apparatus. The control computer 13 has a gradient controller 14 for controlling and switching the magnetic field gradients, and an RF controller 15 for generating and controlling the RF pulses for deflecting the nuclear spins from the steady state. The RF controller 15 may be a multichannel unit that generates RF pulses in a number of independent channels. For example, the imaging sequence required for the acquisition of the MR images may be stored in a memory 16 along with all further control information that is necessary in order to carry out the invention. An image sequence controller 17 controls the image acquisition and consequently, as a function of the chosen imaging sequences, the sequencing of the magnetic field gradients and the RF pulses as well as the reception intervals of the MR signals. Accordingly, the image sequence controller 17 also controls the gradient controller 14 and the RF controller 15. MR images are calculated in a reconstruction computer 20 and may be displayed on a display monitor 18. An operator can control the MR system via an input unit 19. The MR control computer 13, in particular the reconstruction computer 20, is designed (configured) to perform the method described above and in the following.

The non-transitory, computer-readable data storage medium encoded with programming code to perform the method as described can be loaded into and stored in the memory 16 of the MR control computer 13. It is also possible to store the same on a server system or non-centrally.

Figure 2:
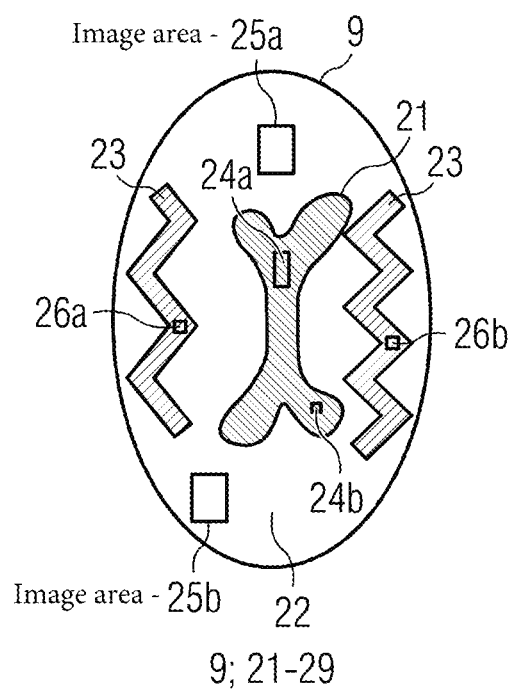
FIG. 2 is a schematic representation of an MR image, in order to explain how the contrast ratio determination may be performed according to the inventive method.

In connection with FIG. 2, it is explained in general terms how the contrast ratio determination may be performed according to the method. For this purpose, FIG. 2 shows the schematic representation of an MR image that used present according to the method and that was generated using an arbitrary measurement protocol. Different intensities can be seen on the image. A transverse scan through a human skull 9 is shown in the schematic representation of FIG. 2. Different anatomical regions are represented schematically, specifically cerebrospinal fluid 21, white matter 22 and gray matter 23. Furthermore, image areas 24a, 24b, 25a, 25b, 26a, 26b marked by boxes are assigned for the purpose of determining the contrast ratios. In this case, 24a and 24b are assigned to regions of the cerebrospinal fluid 21, and 25a and 25b to regions of the white matter 22, and 26a and 26b to regions of the gray matter 23. Contrast ratios KV of different regions $R_a$ and $R_b$ may now be determined from the contrast properties of the first MR image. For example, $KV_{white\ matter}$ and $KV_{gray\ matter}$ may be determined on the basis of the averaging of the intensity densities of the image areas 25a and 25b divided by the averaged intensity density of the image areas 26a and 26b.

Figure 3:
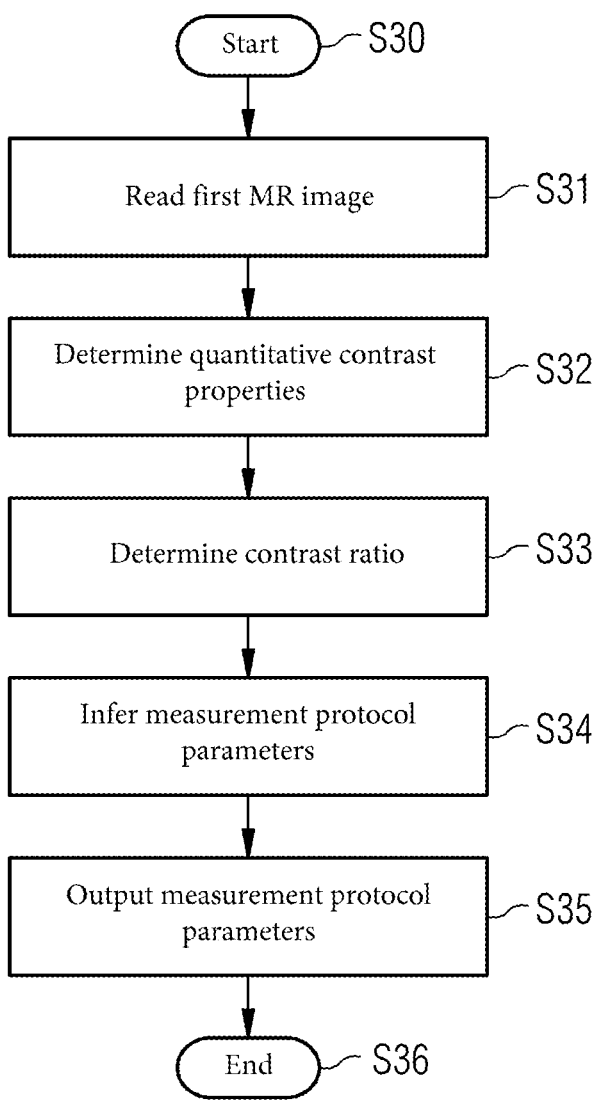
FIG. 3 is a flowchart of the inventive method.

In FIG. 3, the method is summarized in the form of a flowchart. Following the start of the method in step S30, the first MR image is read into the computer in step S31. The quantitative contrast properties are then determined in the computer in a step S32. In step S33, a contrast ratio is now determined from the contrast properties. This may be accomplished in accordance with the description relating to FIG. 2 or based on another suitable method, for example in each case only on the basis of one image area or on the basis of a greater number of image areas which, in addition to the intensity density, may also be weighted according to topographical aspects in the calculation step. In step S34, the measurement protocol parameters that lead to identical or similar contrast properties are inferred from the at least one calculated contrast ratio. Finally, the measurement protocol parameters are output in step S35. The method ends at step S36, and the obtained measurement protocol parameters may be used e.g. for the acquisition of a second MR image.

Figure 4:
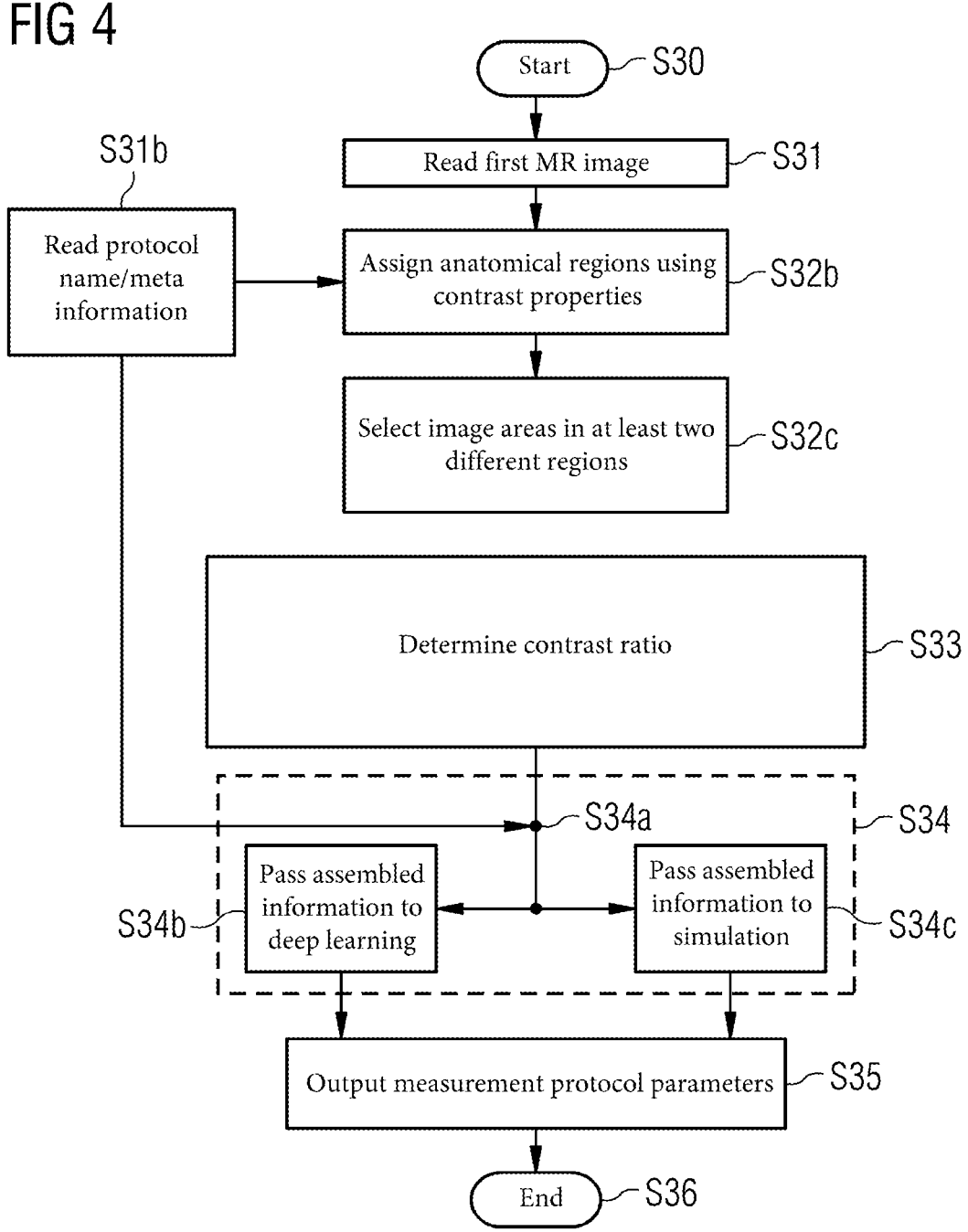
FIG. 4 is a flowchart for a further implementation of the inventive method.

FIG. 4 shows a flowchart for a further implementation of the method. The method starts in step S30 followed by the reading-in of a first MR image in step S31. Protocol name and/or meta information are/is read in additionally in a step S31b. Anatomical regions in the MR image are now assigned in step S32b from the contrast properties, and image areas in at least two different regions $R_a$ and $R_b$ are selected in step 32c.

The intensity density of the regions is used in step S33 in order to calculate a number of contrast ratios that can be assigned to different regions on the basis of the assignment of the image areas to regions. The thus determined contrast ratios are used in step S34 in order to determine the measurement protocol parameters. For this purpose, in a first substep of step S34, in step S34a, the information relating to the contrast ratios may be combined with the protocol name and/or available meta information.

In a second substep of S34, the assembled information is passed to a deep-learning method, step S34b, or to a simulation step, step S34c. A combination of the two substeps is also possible, as indicated by the arrows in FIG. 4.

In step S35, the measurement protocol parameters ascertained in step S34 are emitted as an output. The method accordingly ends at step S36.

Figure 5:
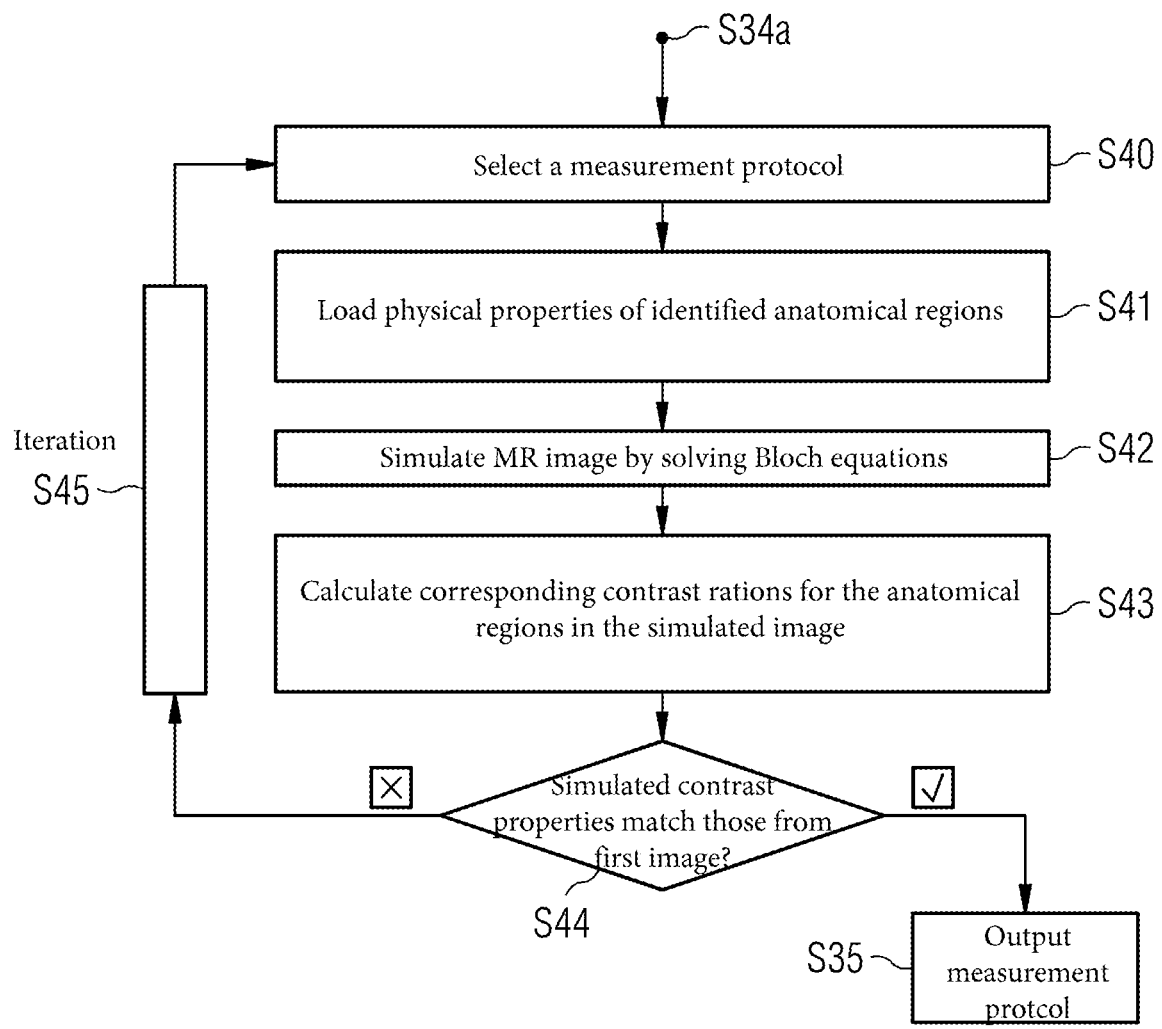
FIG. 5 is a flowchart for a simulation step of the inventive method.

FIG. 5 shows a flowchart for a simulation step. In S34a, the contrast ratios determined for different regions on the basis of the first MR image, as well as protocol name and meta information, if any, are passed to the simulation algorithm. In step S40, the algorithm selects a (test) measurement protocol. On the basis of the identified regions, the physical properties of the identified anatomical regions, for example the $T_1$ and $T_2$ time of the tissue type, are loaded in the next step S41. Using the test measurement protocol, an MR image is simulated in S42 by solving the Bloch equations, and the corresponding contrast ratios for the anatomical regions in the simulated image are calculated in step S43. In a further embodiment variant, contrast ratios are simulated directly. In step S44, the simulated contrast ratios are compared with the contrast ratios that were determined for the first image. If the simulated contrast properties do not match the contrast properties determined from the first image, an iteration of the method takes place. In step S44, the measurement protocol is modified, and the method returns to S40. Passes are made through this loop until a test measurement protocol is determined which fulfills the criterion at S44 or until an abort criterion is reached. In this case, the test measurement protocol is output as the measurement protocol in step S35.

Figure 6:
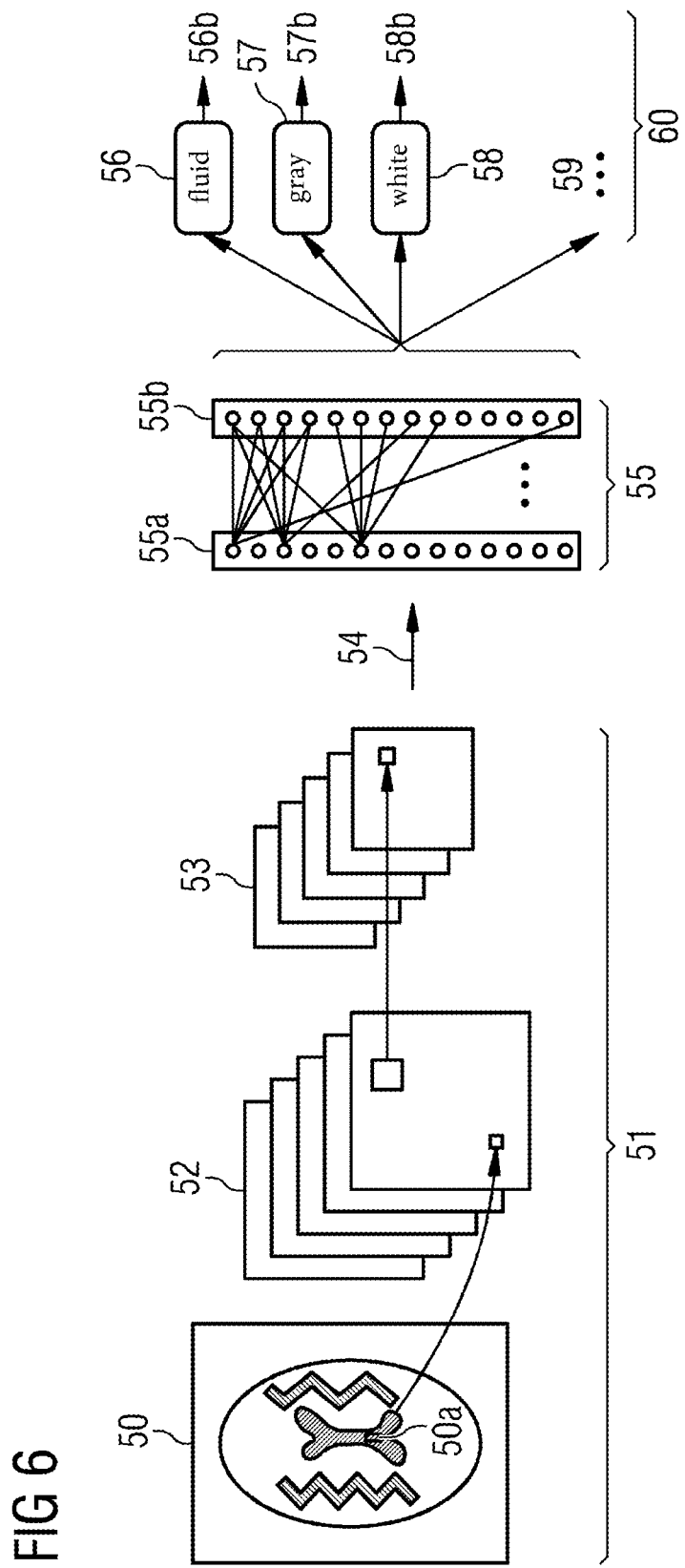
FIG. 6 shows an example of the inventive assignment of image areas to regions by the use of a deep-learning method.

FIG. 6 shows an example of the inventive assignment of image areas to regions by means of a deep-learning method.

For this purpose, a training dataset of acquired MR images is made available. One MR image 50 is shown as an example. Convolution and reduction 51 take place in multiple layers 52, 53 of a neural network. During this process, the information of the image section 50a is reduced in each step. As result 54, interconnected levels 55 are produced (55a, 55b) that enable a binary classification 60. For example, a binary classification of the image section 50a to fluid 56 may be performed, such that a probability $p_{fluid}$ 56b may be specified to indicate whether the image section concerns cerebrospinal fluid. This is possible analogously for gray substance 57, 57b and white substance 58, 58b as well as for further regions 59.

FIG. 7 shows the process for providing a deep-learning network which is suitable for determining measurement protocol parameters for an MR image. For this purpose, a database is created in the first step S70. To that end, MR images 72 are generated by means of measurement protocols 71 or recourse is had to already existing data. By means of region detection in step S73, contrast ratios for anatomical regions are calculated from the MR images in step S74. The combination of measurement protocol 71 and contrast ratios 74 for a multiplicity of data forms the database 75. Optionally, the MR images 72 may be stored in the database 75.

In the second step S76, the deep-learning method is trained by means of the database. For this purpose, a major portion of the database, for example 80% of the available datasets 75a, is used in order to train a deep-learning method in step S77. The result of this process is a trained deep-learning network in step S78. In the validation step S79, the trained network is now applied to the portion of the database 75b not used for the training, and a check is carried out in step S80 to verify whether the network delivers good results, i.e. is capable of determining the measurement protocols. If this is not the case, the training is repeated in step S77 using modified parameters or modified properties of the deep-learning method, for example of the hyperparameters, layer properties, pooling, etc. If the result fulfills the expectations 82, the step is terminated S83 and the network is ready to determine measurement protocol parameters on the basis of contrast properties.

Accordingly, a method is provided by means of which an automatic detection and setting of MR protocols on the basis of read-in image data is possible. This automatic generation of measurement protocol parameters and complete measurement protocols, which achieves an identical contrast on a given scanner, also allows inexperienced users to generate desired contrasts. This enables savings to be made in terms of personnel or service costs, and the reproducibility of MR images across different institutions and scanners to be enhanced.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a magnetic resonance (MR) scanner of an MR apparatus in order to conduct an examination of a subject, said method comprising:
    reading a first MR image, exhibiting first contrast properties, into a computer;
    in said computer, automatically determining a first contrast ratio from said first contrast properties;
    in said computer, determining measurement protocol parameters, using said first contrast ratio, in order to generate, by simulation, a second MR image that exhibits second contrast properties that approximate as closely as possible said first contrast properties; and
    in said computer, generating a measurement protocol comprising control signals corresponding said measurement protocol parameters, and emitting said control signals from said computer to said MR scanner in a form for operating the MR scanner so as to conduct said examination of said subject according to said measurement protocol parameters.

2. A method as claimed in claim 1 wherein said second contrast properties comprise a second contrast ratio in said simulated second MR image, and comprising:
    determining said first contrast ratio from said first contrast properties by identifying at least two first image areas in said first MR image, said at least two image areas being respectively assigned to different regions that are in a list of regions of anatomical features in said first MR image; and
    determining said measurement protocol parameters so as to make said first contrast ratio respectively in each of said at least two first image areas as similar as possible to said second contrast ratio.

3. A method as claimed in claim 2 comprising assigning said at least two first image areas to said list by execution of a deep-learning method in said computer.

4. A method as claimed in claim 1 comprising determining said measurement protocol parameters by executing a deep-learning method in said computer.

5. A method as claimed in claim 4 comprising, in said deep-learning method, accessing a database comprising measurement protocol parameters, contrast properties, and information describing anatomical regions.

6. A method as claimed in claim 1 comprising determining said measurement parameters by simulating a third MR image with third contrast properties therein being simulated iteratively for different measurement protocol parameters until said third contrast properties approximate said first contrast properties as closely as possible.

7. A method as claimed in claim 6 comprising using Bloch equations to simulate said third MR image in said third contrast properties, with knowledge of at least $T_1$ or $T_2$ in anatomical regions identified in said first MR image.

8. A method as claimed in claim 1 comprising determining at least some of said measurement protocol parameters from meta information associated with said first MR image.

9. A method as claimed in claim 1 wherein said first MR image has a protocol name associated therewith, and determining said measurement protocol parameters using said protocol name.

10. A method as claimed in claim 1 comprising reading said first MR image into said computer as a digitized file obtained from a printout, a screen display, or a photograph.

11. A method as claimed in claim 1 wherein said MR scanner that conducts said examination is different from an MR scanner used to generate said first MR image.

12. A method as claimed in claim 1 comprising determining, as said measurement protocol parameters, at least one measurement protocol parameter selected from the group consisting of a field of view, a number of slices of the subject from which MR data are to be obtained, a designation of the MR scanner that is to be used in said examination, a configuration of said MR scanner, a partition of an imaging volume of the subject, a rotation of an imaging volume of the subject, rotational alignment, windowing setting, radio-frequency or gradient pulses to be used in said examination, pre-pulses to be used in said examination.

13. A magnetic resonance (MR) apparatus comprising:
an MR scanner that is to be used to acquire MR data from a subject in an examination;
a computer configured to receive a first MR image, exhibiting first contrast properties, as an input into said computer;
said computer being configured to automatically determine a first contrast ratio from said first contrast properties;
said computer being configured to determine measurement protocol parameters, using said first contrast ratio, in order to generate, by simulation, a second MR image that exhibits second contrast properties that approximate as closely as possible said first contrast properties; and
said computer being configured to generate a measurement protocol comprising control signals corresponding said measurement protocol parameters, and to emit said control signals from said computer to said MR scanner in a form for operating the MR scanner so as to conduct said examination of said subject according to said measurement protocol parameters.

14. A non-transitory, computer-readable data storage medium encoded with programming instructions, said storage medium being loaded into a computer of a magnetic resonance (MR) apparatus comprising an MR scanner to be used to conduct an examination of a subject, and said programming instructions causing said computer to:
receive a first MR image, exhibiting first contrast properties;
determine a first contrast ratio from said first contrast properties;
determine measurement protocol parameters, using said first contrast ratio, in order to generate, by simulation, a second MR image that exhibits second contrast properties that approximate as closely as possible said first contrast properties; and
generate a measurement protocol comprising control signals corresponding said measurement protocol parameters, and emit said control signals from said computer to said MR scanner in a form for operating the MR scanner so as to conduct said examination of said subject according to said measurement protocol parameters.

* * * * *